US00PP26589P3

(12) United States Plant Patent
Suphachadiwong

(10) Patent No.: US PP26,589 P3
(45) Date of Patent: Apr. 5, 2016

(54) *VANDA* ORCHID PLANT 'SPCDW1203'

(50) Latin Name: *Vanda* hybrid
Varietal Denomination: SPCDW1203

(71) Applicant: Thumrong Suphachadiwong, Chonburi (TH)

(72) Inventor: Thumrong Suphachadiwong, Chonburi (TH)

(73) Assignee: Suphachatwong Innovation (TH)

( * ) Notice: Subject to any disclaimer, the term of this patent is extended or adjusted under 35 U.S.C. 154(b) by 187 days.

(21) Appl. No.: 13/987,374

(22) Filed: Jul. 17, 2013

(65) Prior Publication Data

US 2015/0026850 P1 Jan. 22, 2015

(30) Foreign Application Priority Data

Jul. 17, 2012 (QZ) ..... PBR 2012/1586

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

CPVO Community Plant Variety Office, Official Gazette of the Community Plant Variety Office 15/10/2012, pp. 37 and 55.*

* cited by examiner

*Primary Examiner* — June Hwu
(74) *Attorney, Agent, or Firm* — Cassandra Bright

(57) ABSTRACT

A new and distinct *Vanda* cultivar named 'SPCDW1203' is disclosed, characterized by unique petal coloration of greyed-orange with greyed-red spots and stripes. The plant shows a strong tolerance of cold temperatures, for the Genus. The new variety is a *Vanda*, typically produced as an indoor ornamental plant.

1 Drawing Sheet

Latin name of the genus and species: *Vanda* hybrid.
Variety denomination: 'SPCDW1203'.

BACKGROUND OF THE INVENTION

This application relates to a new cultivar of *Vanda*, as described in EU application number 2012/1586, filed Jul. 17, 2012, grant pending, to which applicant claims priority. The new variety is the product of a planned breeding program. The new variety originated as a seedling from the crossing of the unpatented, proprietary seed parent *Vanda* 'TKJL' with the unpatented, proprietary pollen parent referred to as *Vanda* 'D2JK'. The crossing was made by the inventor in his research greenhouse in Chonburi, Thailand in June of 2001.

The new variety was first selected by the inventor, Thumrong Suphachadiwong, a citizen of Thailand, in May of 2006, in a research greenhouse belonging to the inventor in Chonburi, Thailand. After identifying the new variety as a potentially interesting selection, the inventor continued confidential testing and propagation of 'SPCDW1203', assessing stability of the unique characteristics of this variety.

Asexual reproduction of the new cultivar 'SPCDW1203' was first performed at a commercial laboratory belonging to the inventor in Chonburi, Thailand by tissue culture, using tissue from the base of the foliage, in June of 2006. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type. *Vanda* propagation can be done by taking a cutting of a tip off a plant. A plant will have aerial roots, and some of these aerial roots emerge from a branch of the orchid plant between sets of leaves. Cut off the tip of the plant just below where these roots emerge, and you will have a cutting that already has aerial roots.

SUMMARY OF THE INVENTION

The cultivar 'SPCDW1203' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1203'. These characteristics in combination distinguish 'SPCDW1203' as a new and distinct *Vanda* cultivar:

1. Unusual greyed-orange petal color with greyed-red spots and stripes.
2. Durable foliage.
3. Good tolerance for cold temperatures, for the Genus
4. Ligulate, foliage which is strongly carinate and slightly curved in aspect.

PARENT COMPARISON

Plants of the new cultivar 'SPCDW1203' are similar to the seed parent, *Vanda* in most horticultural characteristics. The new variety, however, produces larger flowers than the seed parent.

Plants of the new cultivar 'SPCDW1203' are similar to the pollen parent, *Vanda* in most horticultural characteristics. Plants of the new variety, however, are more compact than the pollen parent.

COMMERCIAL COMPARISON

'SPCDW1203' is similar in most horticultural characteristics to the unpatented commercial variety *Vanda* 'Sunanda Magic Gold' in most horticultural characteristics. The new variety, however, produces sepals and petals colored orange with brown spots, whereas 'Sunanda Magic Gold' produces petals and sepals that are yellow with brown spots. The brown spots found on petals and sepals of 'SPCDW1203' are larger than those found on 'Sunanda Magic Gold'. The new variety has a flower with a different lip shape, and different dorsal sepals than 'Sunanda Magic Gold'. Additionally, the flower size of the new variety is smaller than that of 'Sunanda Magic Gold'.

BRIEF DESCRIPTION OF THE PHOTOGRAPH

The accompanying photograph in FIG. 1 illustrates in full color a typical plant of 'SPCDW1203' grown in a commercial greenhouse in Honselersdijk, the Netherlands. This plant is approximately 3 years old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1203' plants grown in a greenhouse in Honselersdijk, the Netherlands. Temperatures ranged were approximately 23° C. during the day and 19° C. at night. No photoperiodic or chemical treatments were given to the plants. When natural lighting fell below 150 Watt, artificial lighting is given at 10,000 lux for 16 hours a day. Measurements and numerical values represent averages of typical plant types.

Botanical classification: *Vanda* hybrid 'SPCDW1203'.

PROPAGATION

Type of propagation typically used: Tissue culture.

Propagation details: The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

Root description: Moderately to heavy rooting with aerial roots only. Roots are very fleshy, non-fibrous.

- *Location of roots.*—Base of the stem, growing from approximately the lowest 20% of the stem.
- *Average length of mature roots.*—25 cm.
- *Average diameter of roots.*—Old Roots: 2 mm. Young Roots: 4.5 mm.
- *Old roots colored yellow-green.*—Near RHS Grey-Green 196B.
- *Young roots colored greyed-green.*—Near RHS 191A.

PLANT

Growth habit: Monopodial, upright.

Height from soil line to top of foliage: Average height from base (plant grown in hanging basket, so no soil line present) to top of foliage: 25 cm.

Height from soil line to top of flowers: Average height from base (plant grown in hanging basket, so no soil line present) to top of foliage: 40 cm.

Stem diameter: Average 1.0 cm.

Plant spread: Average: 35 cm.

Normal pot size: Hanging basket (8×8 cm square).

Growth rate: Moderate.

Number of leaves per plant: Average: 20.

FOLIAGE

- *Average length.*—Approximately 18 cm.
- *Average width.*—Approximately 2.9 cm.
- *Shape of blade.*—Ligulate, carinate, slightly twisted lengthways.
- *Aspect.*—Very slightly curved.
- *Apex.*—Unequal emarginated to unequal praemorse.
- *Base.*—Sheathing. Sheath length: Average 2.0 cm. Sheath width: Average 1.2 cm. Sheath color: Yellow-green; near RHS 144A.
- *Margin.*—Entire.
- *Texture of top surface.*—Smooth, dull.
- *Texture of bottom surface.*—Smooth, dull.
- *Color.*—Young foliage upper side: Near RHS Green 137B. Young foliage under side: Near RHS Green 143A. Mature foliage upper side: Near RHS Green 137A. Mature foliage under side: Near RHS Green 137A.
- *Venation.*—Type: Parallel. Venation coloration: Green; near RHS N137B.

Petiole: No petioles present, leaves sessile.

FLOWERING CHARACTERISTICS

Flower bud:

- *Length.*—Average: 1.8 cm.
- *Diameter.*—Average: 1.9 cm.
- *Shape.*—Broad ovate to near pyramidal.
- *Color.*—Yellow-green; in between near RHS 145A and 147D, tinged greyed-orange; near RHS 174A and 174B, especially towards the tip.

Peduncle:

- *Length.*—Approximately 34.5 cm.
- *Angle.*—Approximately 40° angle to main stem.
- *Strength.*—Very strong.
- *Texture.*—Glabrous, rounded, matte.
- *Color.*—Yellow-green; near RHS 144A to 144B.

INFLORESCENCE

- *Flowers per stem.*—Average: 5 to 7.
- *Inflorescence arrangement.*—Axially placed raceme.
- *Inflorescence height.*—Approximately 19 cm (measured from base of lowest flower to top of upper flower).
- *Inflorescence width.*—Approximately 14 cm.
- *Inflorescence orientation.*—Obliquely upward.

INDIVIDUAL FLOWERS

- *Flower type.*—Zygomorphic (orchidaceous), typical shape for the genus *Vanda*.

*Shape.*—Zygomorphic, consisting of three sepals and three petals, one of which is transformed into a labellum (lip).
*Flower orientation.*—Outward; towards all directions.
*Length (height).*—Approximately 9 cm.
*Width.*—Approximately 11 cm.
*Depth.*—Approximately 4.2 cm.
*Fragrance.*—No fragrance.
*Persistent.*—No.
*Quantity of petals.*—3 (2 "traditional" petals and a labellum (lip), described separately).
*Lastingness of flower on plant.*—Each individual flower can stay on the spike up to 6 weeks, counted from the day of opening of the flower until the day the flower drops. The actual lastingness of flowers depends on several external circumstances.

Petals:
*Arrangement.*—One lateral petal on each side.
*Length.*—Approximately 5.2 cm.
*Width.*—Approximately 4.6 cm.
*Shape.*—Broad ovate.
*Apex.*—Obtuse.
*Base.*—Cuneate.
*Margin.*—Entire, wavy.
*Margin color.*—Greyed-red; near RHS 181A and 181B.
*Texture.*—Upper forward surface: Smooth, dull, velvety.
*Texture.*—Lower back surface: Smooth, dull, velvety.
*Color.*—When opening, forward surface: Near RHS Greyed-Orange 175B. When opening, back surface: Near RHS Greyed-Orange 175D. Fully Opened, forward surface: Near RHS Greyed-Orange 164C background color, stripes and spots near Greyed-Orange 175A. Fully Opened, back surface: Near RHS Greyed-Orange 164D background color, faint stripes and spots near Greyed-Orange 172A. Fading, forward surface: Not fading. Fading, back surface: Not fading.

Labellum/lip:
*Shape.*—Three-lobed, lateral lobes involute, central lobe bi-lobed, with revolute margins.
*Length.*—Approximately 2 cm.
*Width.*—Approximately 1.2 cm.
*Texture.*—Smooth, dull, with 3 callosities.
*Tip.*—Bi-lobed.
*Base.*—Cuneate.
*Color.*—When opening, forward surface: Lateral lobes are yellow (near RHS 13A), tinged orange-red (near RHS 31A). Central lobe and callosities are red (near RHS 46A), orange-red base (near RHS 31B). When opening, back surface: Lateral lobes yellow (near RHS 13B to 13C), central lobe orange (near RHS 29A to 29B), upper half red (near RHS 46A). Fully Opened, forward surface: Lateral lobes yellow (near RHS 13A), tinged orange-red (near RHS 31A). Central lobe and callosities red (near RHS 46A), orange-red base (near RHS 31B). Fully Opened, back surface: Lateral lobes yellow (near RHS 13B to 13C), central lobe orange (near RHS 29A to 29B), upper half red (near RHS 46A). Fading, forward surface: Not fading. Fading, back surface: Not fading.
*Color venation fully opened, forward surface.*—No venation visible on labellum.
*Color venation fully opened, back surface.*—No venation visible on labellum.
*Margin.*—Entire.

Spurs:
*Quantity.*—Average: 1.
*Length.*—Approximately 0.5 cm.
*Width.*—Approximately 0.2 cm.
*Height.*—Approximately 0.4 cm.
*Shape.*—Short triangular, in line with central lobe of labellum.
*Apex.*—Obtuse.
*Base.*—Broad cuneate.
*Margin.*—Entire.
*Texture.*—Smooth, slightly glossy.
*Color.*—Near RHS Greyed-Red 178C.
*Type.*—Short triangular.

Sepals:
*Quantity.*—Average: 3; One dorsal sepal (pointing upright) and two lateral sepals.
*Length.*—Dorsal sepal approximately 5 cm. Lateral sepals approximately 6 cm.
*Width.*—Dorsal sepal approximately 5 cm. Lateral sepals approximately 5.5 cm.
*Shape.*—Broad ovate.
*Apex.*—Obtuse.
*Base.*—Cuneate.
*Margin.*—Entire, wavy.
*Texture.*—Smooth, dull.
*Color.*—Dorsal sepal upper side: Orange and greyed-red, 29B, 29C, 179C and 179D, darker towards the top; near RHS 181B to 181C, sepal heavily dotted greyed-purple; 185A and with many small dots coloured red; near RHS 57D. Dorsal sepal under side: Greyed-orange; 164C and 165D, margins and top greyed-red; near RHS 180A and 180B, moderately veined and dotted greyed-red; near RHS 180B and 180C. Lateral sepal upper side: Yellow-orange; 22B to 22D, darker towards the top; near RHS 181A to 181B, sepal very heavily dotted and veined greyed-purple; 183B to 183C and 184A to 184B. Lateral sepal under side: Greyed-orange; 164C and 165D, margins and top greyed-red; near RHS 180A and 180B, moderately veined and dotted greyed-red; near RHS 180B and 180C.

Pedicels:
*Length.*—Approximately 4 cm.
*Diameter.*—Approximately 0.5 cm.
*Angle.*—Approximately 65° angle to peduncle.
*Strength.*—Very strong.
*Texture.*—Smooth, axially angled with 5 "ribs", axially twisted (due to resupination), glossy.
*Color.*—Near RHS Greyed-Orange 164C.

REPRODUCTIVE ORGANS

*Stamens, style and stigma fused into column?.*—Yes.
*Column length.*—Approximately 0.6 cm.
*Column diameter.*—Approximately 0.5 cm.
*Column color.*—Near RHS White 155A.
*Ovary.*—Position: Inferior. Diameter: Approximately 0.5 cm. Color: Violet; near 85A.
*Pollinia color.*—Near Yellow 15A.

OTHER CHARACTERISTICS

Disease resistance: Good resistance to the normal diseases found in *Vanda*.
Drought tolerance and cold tolerance: Drought tolerance is typical for species. Superior cold tolerance, to approximately 6 degrees Celsius.
Fruit/seed production: No fruits/seeds detected to date.

What is claimed is:

1. A new and distinct cultivar of *Vanda* plant named 'SPCDW1203' as herein illustrated and described.

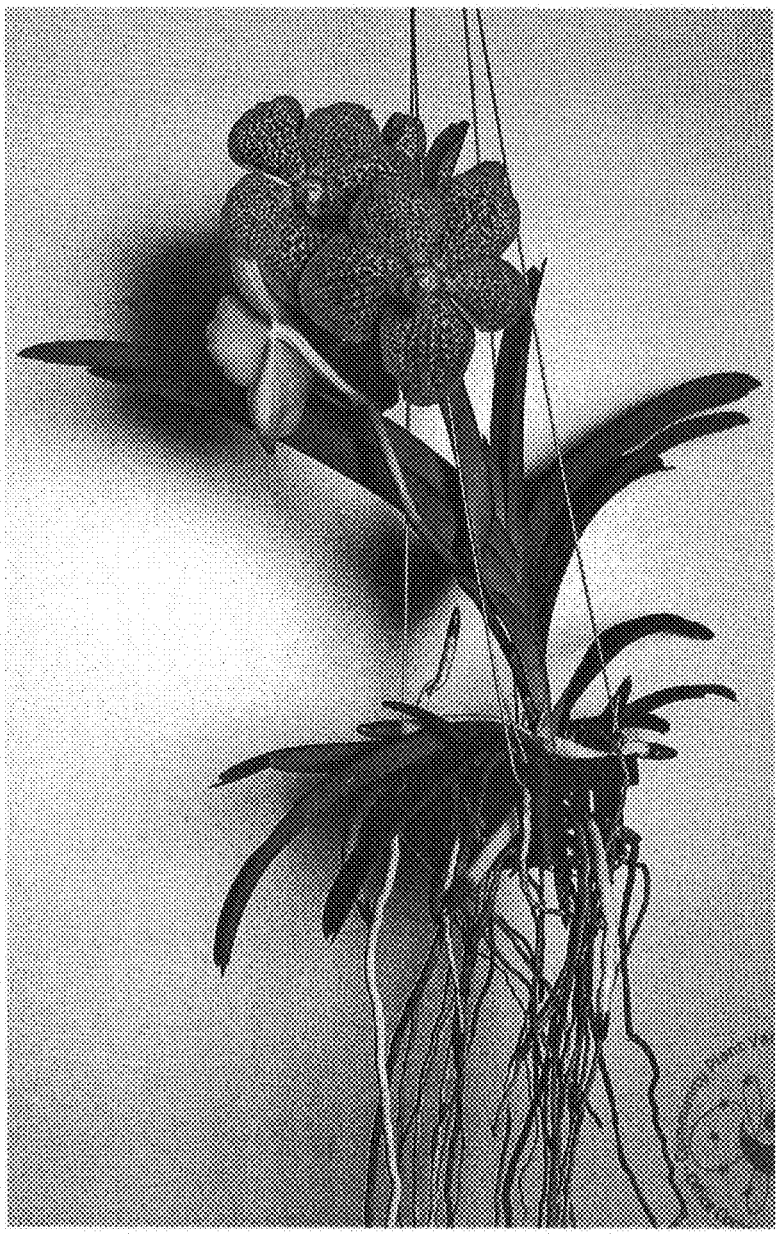

* * * * *